United States Patent
Indolese

(10) Patent No.: US 6,420,608 B1
(45) Date of Patent: Jul. 16, 2002

(54) PROCESS FOR THE PREPARATION OF TRIFLUOROMETHYL ACETOPHENONE

(75) Inventor: Adriano Indolese, Möhlin (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/446,233

(22) PCT Filed: Jun. 17, 1998

(86) PCT No.: PCT/EP98/03639

§ 371 (c)(1),
(2), (4) Date: Dec. 16, 1999

(87) PCT Pub. No.: WO98/58895

PCT Pub. Date: Dec. 30, 1998

(30) Foreign Application Priority Data

Jun. 19, 1997 (GB) .............................................. 9712999

(51) Int. Cl.$^7$ .............................................. C07C 45/45
(52) U.S. Cl. ...................................... 568/322; 568/323
(58) Field of Search .................................. 568/322, 323

(56) References Cited

PUBLICATIONS

J. Org. Chem. 1987, 52, pp. 3529–3536, Anderson et al., 'Regiochemistry of palladium–catalyzed arylation reactions of enol ethers. Electronic control of selection for alpha–or beta–arylation.'.*

* cited by examiner

Primary Examiner—Brian J. Davis
(74) Attorney, Agent, or Firm—Joseph C. Gil

(57) ABSTRACT

A process for the preparation of a compound of formula I

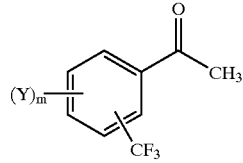

I wherein Y is a group that is inert during preparation of the compound and m is from 0 to 4 is described. The process broadly involves the steps of a) reacting a compound of formula II

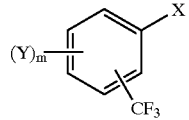

II wherein X is chlorine, bromine or iodine, and Y and m are as defined above, with a vinylether or an enamide in a solvent, a base and a catalytic amount of a palladium compound and a phosphine ligand. The resulting intermediate is then hydrolyzed to the compound of formula I.

17 Claims, No Drawings

PROCESS FOR THE PREPARATION OF TRIFLUOROMETHYL ACETOPHENONE

This application is a 371 of PCT EP98/03639 filed Jun. 17, 1998.

The invention relates to a process for the preparation of trifluoromethyl acetophenone derivatives of formula I

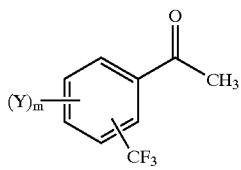

I wherein:
  Y is a group that is inert for the reactions, preferably a hydrocarbyl; and
  m is from 0 to 4; preferably 0; in which process
  a) a compound of formula II

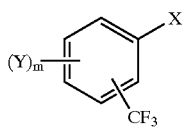

II wherein
  X is chlorine, bromine or iodine, preferably bromine, and
  Y and m are as defined for formula I,
  is reacted with a vinylether of formula IIIa or an enamide of formula IIIb

(IIIa)

(IIIb)

wherein $R_1$ and $R_2$ are each independently of the other $C_1$–$C_8$alkyl, $C_2$–$C_8$alkenyl, $C_1$–$C_8$alkoxyalkyl, $C_3$–$C_6$cycloalkyl, phenyl-$C_{1-C2}$alkyl or $C_1$–$C_8$acyl, which groups are optionally substituted,
  $R_3$ is $C_1$–$C_8$alkyl, $C_2$–$C_8$alkenyl, $C_1$–$C_8$alkoxyalkyl, $C_3$–$C_6$cycloalkyl or phenyl-$C_1$–$C_2$alkyl, which groups are optionally substituted,
  in a solvent, in the presence of a base and of a catalytic amount of a palladium compound comprising a monodental or bidental phosphine ligand;
  b) the resulting intermediate of formula IVa and IVb resp.

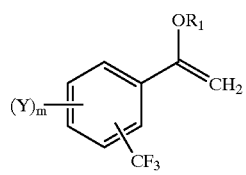

IVa

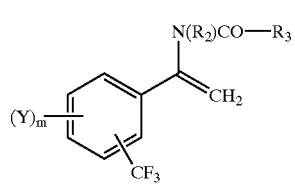

IVb is hydrolyzed to the compound of formula I.

These compounds are important intermediates for the preparation of pharmaceuticals, pesticides, dyestuffs, perfumes and other products.

The palladium catalyzed vinylation of aromatic halogen compounds is the well known "Heck"-reaction. In this reaction, vinyl ethers can react in (a) or in (b) position, resulting in compounds A and B respectively, as shown the scheme 1. Only compound A can be hydrolyzed to the acetophenone C. Thus, for the preparation of acetophenones by the "Heck"-reaction, the initial vinylation reaction should predominantly occur in (a) position.

Scheme 1

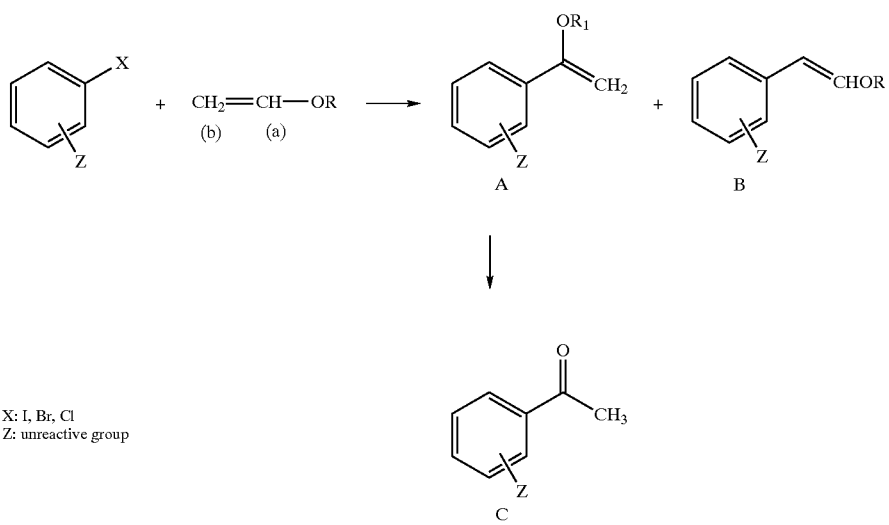

X: I, Br, Cl
Z: unreactive group

EP-A-688,757 discloses the vinylation of halogen benzene derivatives in the presence of a palladium/phosphine catalyst; the regioselectivity of the reaction with respect to the vinyl group is not discussed therein, but according to the working examples the vinyl group reacts predominantly in (b) position. The preparation of acetophenones by palladium catalyzed reaction of aryl halides with vinyl ethers is described in J. Org. Chem. Vol.52, 1987, 3529–3536. The regioselectivity of this reaction is dependent, amongst others, on the catalyst and the substituent on the aryl group. Substitution at (a)-position is increased by adding phosphine ligands to the palladium catalyst (J. Org. Chem. Vol.57, 1992, 1481–1486), whereas electron withdrawing groups on the aryl moiety favour substitution at (b)-position (J. Org. Chem. Vol.52, 1987, 3529–3536). Accordingly, the strongly electron withdrawing trifluoromethyl group is expected to favour substitution at (b)-position over (a)-position resulting in low yields of trifluoromethyl acetophenone. Surprisingly it has been found that a high ratio of (a)-substitution over (b)-substitution can be obtained in the reaction according to this invention, resulting after hydrolysis in good yields of the corresponding trifluoromethyl acetophenone. The method provided herewith is distinguished by ready availability of the starting materials, good technical feasibility and is economically and ecologically favorable. The groups $R_1$, $R_2$ and $R_3$ may be substituted by any functional group which does not negatively affect the reaction; examples are $C_1$–$C_8$alkyl, halo-$C_1$–$C_8$alkyl, $C_2$–$C_8$alkenyl, halo-$C_2$–$C_8$alkenyl, $C_1C_8$alkoxyalkyl, $C_3$–$C_6$cycloalkyl, phenyl, phenoxy, phenyl-$C_1$–$C_2$alkyl, hetaryl, hetaryloxy or $C_1$–$C_8$acyl.

Suitable palladium compounds which can be used as catalysts are for example palladium bis-(dibenzalacetone)-palladium, palladium acetate, palladium dichloride, palladium dibromide, palladium trifluoroacetate, palladium diphosphine halogenide complexes and acetate complexes as palladium-bis(triphenylphosphine) dichloride and palladium-bis(triphenylphosphine) acetate; further on palladium tetrachloro complexes; preferred is bis-(dibenzalacetone)-palladium. Suitable phosphine ligands are aryl phosphines as triphenyl phosphine, methyl diphenylphosphine or 1,3-bis-(diphenylphosphino)-propane, preferably triphenyl phosphine. The amount of palladium catalyst is 0.01 to 10 mol %, preferably 0.1 to 1 mol % in relation to the compound of formula II.

The molar ratio of palladium to phosphine is from 1:1 to 1:4, preferably ca. 1:2.

Suitable solvents for reaction step a) are aprotic, polar solvents, preferably propylene carbonate, anisole, N-methyl-2-pyrrolidone, N,N-dimethyl acetamide, dimethylformamide, tetramethylurea, gamma-butyrolacone, N,N-dimethylimidazolidinon and dimethyl sulfoxide.

Suitable bases are amines, as triethylamine, triethylenediamine, cyclohexylamine, N-cyclohexyl-N,N-dimethyl-amine, N,N-diethylaniline, pyridine, 4-(N,N-dimethylamino)pyridine, N-methylmorpholine and 1,8-diazabicyclo[5.4.0]undec-5-ene (DBU); alkali metal or alkaline earth metal hydroxides, carbonates, hydrogencarbonates and phosphates, preferably potassium salts; or salts of carboxylic acids, preferably alkali salts of $C_2$–$C_4$carboxylic acids. Preferred are triethylamine, potassium hydroxide, -carbonate,-hydrogencarbonate and -phosphate, and sodium acetate; particularly preferred is triethylamine.

Reaction step a) is carried out at from 50° C. to 200° C., preferably from 70° C. to 150° C.; most preferably from 90° C. to 120° C. Reaction step b) (hydrolysis) is carried out with diluted acid, as hydrochloric acid, sulfuric acid or acetic acid, preferably in mixture with a solvent, wherein the product is soluble. The temperature is not critical and may vary from 0° C. to +70° C.

Preferred is the preparation of 3-trifluoromethylacetophenone, wherein 3-bromo-benzotrifluorid is reacted with a vinylether of formula IIIa

$$CH_2=CH—OR_1 \qquad (IIIa)$$

wherein $R_1$ is $C_1$–$C_8$alkyl; preferably $C_4$–$C_6$alkyl.

PREPARATION EXAMPLES

Example 1

3-Trifluoromethyl-1-butoxystyrene a) To 22.5 g (100 mmol) 3-bromo-benzotrifluoride and 80 ml propylene carbonate under argon 20.2 g (200 mmol) triethyl amine, 20.0 g (200 mmol) butyl vinyl ether, 518 mg (0.5 mmol) bis-(dibenzalacetone)-chloroform-palladium and 525 mg (2 mmol) triphenyl phospine are added. The reaction mixture is heated to 110° C. for 20 hours, cooled to room temperature and filtered. The filtrate is extracted twice with 50 ml hexane. The hexane phase is washed twice with 50 ml water, dried with $Na_2SO_4$ and the solvent is evaporated. 26 g of an oil are obtained that contains 21 g of 3-trifluoromethyl-1-butoxystyrene (yield 80%).

b) To 22.5 g (100 mmol) 3-bromo-benzotrifluoride, potassium carbonate (200 mmol) and 80 ml propylene carbonate under argon 20.0 g (200 mmol) butyl vinyl ether, 518 mg (0.5 mmol) bis-(dibenzalacetone)-chloroform-palladium and 788 mg (3 mmol) triphenyl phospine are added. The reaction mixture is heated to 140° C. for 20 hours, cooled to room temperature and filtered. The filtrate is extracted twice with 50 ml hexane. The hexane phase is washed twice with 50 ml water, dried with $Na_2SO_4$ and the solvent is evaporated. 26 g of an oil are obtained that contains 20 g of 3-trifluoromethyl-1-butoxystyrene (yield 77%).

Example 2

3-Trifluoromethyl-acetophenone

To 26 g of raw 3-trifluoromethyl-1-butoxystyrene (80 mmol) 30 ml N,N-dimethylformamide and 30 ml 1 M hydrochloric acid are added and the mixture is stirred for 10 hours at room temperature. 100 ml water are added and the mixture is extracted twice with 100 ml methylene chloride. The organic phase is washed with 50 ml water, dried with $Na_2SO_4$, and the solvent evaporated under reduced pressure. The residue is destined to give 11 g trifluoromethyl-acetophenone (bp. 96° C./50 mbar, 73% yield).

Example 3

3-Trifluoromethyl-1-ethoxystyrene

To 22.5 g (100 ml) of 3-bromo-benzotrifluoride and 80 ml propylene carbonate under argon 20.2 g (200 mmol) triethyl amine, 14.4 g (200 mmol) ethyl vinyl ether, 518 mg (0.5 mmol) bis-(dibenzalacetone)-chloroform-palladium and 525 mg (2 mmol) triphenyl phospine are added. The reaction mixture is heated in an autoclave to 120° C. for 20 hours, cooled to room temperature, filtered and the filtrate extracted twice with 50 ml hexane. The hexane phase is washed twice with 50 ml water, dried with $Na_2SO_4$ and the solvent is evaporated. The residue is distilled to give 16 g 3-trifluoromethyl-1-ethoxystyrene (b.p. 113° C./50 mbar, yield 75%). Hydrolysis according to Example 2 results in trifluoromethyl-acetophenone (76% yield).

Example 4

Different Phosphine to Palladium Ratios

3-Trifluoromethyl-1-butoxystyrene 26 mg (0.025 mmol) bis-(dibenzalacetone)-chloroform-palladium and different amounts of triphenyl phosphine are placed in a Schlenk-tube under argon. 4 ml propylene carbonate, 1.12 g (5 mmol) 3-bromo-benzotrifluoride 0.76 g (7.5 mmol) triethyl amine and 0.75 g (7.5 mmol) butyl vinyl ether are added. The reaction mixture is heated to 120° C. for 20 hours. It is cooled to room temperature and 200 mg hexadecane (internal standard) and 15 ml diethyl ether are added. The mixture is analysed by GC.

| Pd:P | conversion/% | yield/% | (a)-selectivity/% |
|---|---|---|---|
| 1:1 | 75 | 44 | 86 |
| 1:2 | 98 | 81 | 87 |
| 1:3 | 87 | 73 | 89 |
| 1:4 | 67 | 56 | 92 |

Example 5

Different Solvents

3-Trifluoromethyl-1-butoxystyrene 26 mg (0.025 mmol) bis-(dibenzalacetone)-chloroform-palladium and 27mg (0.1 mmol) triphenyl phosphine are placed in a Schlenk-tube under argon. 4 ml solvent, 1.12 g (5 mmol) 3-bromo-benzotrifluoride 0.76 g (7.5 mmol) triethyl amine and 0.75 g (7.5 mmol) butyl vinyl ether are added. The reaction mixture is heated to 120° C. for 20 hours. It is cooled to room temperature and 200 mg hexadecane (internal standard) and 15 ml diethylether are added. The mixture is analysed by GC.

| solvent | conversion/% | yield/% | (a)-selectivity/% |
|---|---|---|---|
| (none) | 26.6 | 21.1 | 79.4 |
| anisole | 100.0 | 64.3 | 74.5 |
| N-methyl-pyrrolidone | 75.4 | 55.3 | 83.1 |
| N,N-dimethyl-acetamide | 72.8 | 54.2 | 84.9 |
| propylene carbonate | 98.8 | 81.8 | 86.9 |

Example 6

Different Ligands

3-Trifluoromethyl-1-butoxystyrene 26 mg (0.025 mmol) bis-(dibenzalacetone)-chloroform-palladium and 0.1 mmol of a ligand are placed in a Schlenk-tube under argon. 4 ml N,N-dimethyl-acetamide, 1.12 g (5 mmol) 3-bromo-benzotrifluoride 0.76 g (7.5 mmol) triethyl amine and 0.75 g (7.5 mmol) butyl vinyl ether are added. The reaction mixture is heated to 120° C. for 20 hours. It is cooled to room temperature and 200 mg hexadecane (internal standard) and 15 ml diethylether are added. The mixture is analysed by GC.

| ligand | conversion/% | yield/% | (a)-selectivity/% |
|---|---|---|---|
| triphenyl phosphine | 72.8 | 54.2 | 84.9 |
| methyl-diphenylphosphine | 23.1 | 21.4 | 92.6 |
| 1,3-bis-(diphenylphoshino)-propane | 3.1 | 1.7 | 54.0 |

Example 7

Preparation of 3-bromo-benzotrifluoride (educt)

3280 g of bromine are added to a mixture of 6046 g benzotrifluoride, 68 g $FeCl_3$ and 2 g $SiO_2$ at about 20° C. within ca. 2 hours. The reaction temperature is then slowly rised within ca. 7 hours to ca 40° C., 300 g water and 130 g $Na_2S_2O_3$ are added and stirred for ca. 15 minutes. The phases are separated and the organic phase is destilled resulting in 4160 g bromo-benzotrifluoride (isomeric ratio 3:4=96:4) and 3290 g benzotrifluoride which is recycled.

What is claimed is:

1. A process for the preparation of a compound of formula I

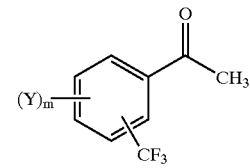

wherein:
  Y is a hydrocarbyl group that is inert during preparation of the compound; and
  m is from 0 to 4; in which process
  a) a compound of formula II

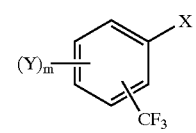

wherein
  X is chlorine, bromine or iodine, and
  Y and m are as defined for formula I,
  is reacted with a vinylether of formula IIIa or an enamide of formula IIIb $$CH_2=CH-OR_1 \quad \text{(IIIa)}$$

$$CH_2=CH-N(R_2)-CO-R_3 \quad \text{(IIIb)}$$

wherein
  $R_1$ and $R_2$ are each independently of the other $C_1$–$C_8$alkyl, $C_2$–$C_8$alkenyl, $C_1$–$C_8$alkoxyalkyl, $C_3$–$C_6$cycloalkyl, phenyl-$C_1$–$C_2$alkyl or $C_1$–$C_8$acyl, and
  $R_3$ is $C_1$–$C_8$alkyl, $C_1$–$C_8$alkenyl, $C_1$–$C_8$alkoxyalkyl, $C_3$–$C_6$cycloalkyl or phenyl-$C_1$–$C_2$alkyl, in a solvent, in the presence of a base and of a catalytic amount of a palladium compound and a monodental or bidental phosphine ligand;

b) the resulting intermediate of formula IVa and IVb

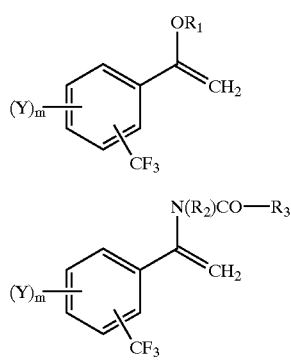

is hydrolyzed to the compound of formula I.

2. A process according to claim 1, wherein the palladium compound is selected from bis-(dibenzalacetone)-palladium, palladium acetate, palladium dichloride, palladium dibromide, palladium trifluoroacetate, palladium diphosphine halogenide complexes and acetate complexes, palladium tetrachloro complexes.

3. A process according to claim 1, wherein the phosphine ligand is an aryl phosphine.

4. A process according to claim 3, wherein the phosphine ligand is selected from triphenyl phosphine, methyl diphenylphosphine and 1,3-bis-(diphenylphosphino)-propane.

5. A process according to claim 1, wherein the amount of palladium compound is 0.01 to 10 mol %, in relation to the compound of formula II.

6. A process according to claim 1, wherein the molar ratio of palladium to phosphine is from 1:1 to 1:4.

7. A process according to claim 1, wherein the solvent for reaction step a) is an aprotic, polar solvent.

8. A process according to claim 1, wherein the base is selected from amines, alkali metal or alkaline earth metal hydroxides, -carbonates, -hydrogencarbonated and -phosphated; and salts of carboxylic acids.

9. A process according to claim 1, wherein reaction step a) is carried out at 50° C. to 200° C.; and reaction step b) is carried out at 0° C. to 70° C.

10. A process according to claim 1 for the preparation of 3-trifluoromethylacetophenone, wherein 3-bromobenzotrifluorid is reacted with a vinylether of formula IIIa

wherein $R_1$ is $C_1$–$C_8$alkyl.

11. The process of claim 1 wherein the palladium compound is bis-(dibenzalacetone)-palladium and the phosphine ligand is triphenyl phosphine.

12. The process of claim 5 wherein the amount of palladium compound is 0.1 to 1 mol % in relation to the compound of formula II and wherein the molar ratio of palladium compound to phosphine ligand is about 1.2.

13. The process of claim 7 wherein the solvent is elected from the group consisting of propylene carbonate, anisole, N-methyl-2-pyrrolidone, N,N-dimethyl acetamide, dimethylformamide, tetramethylurea, gamma-butyrolacone, N,N-dimethylimidazolidinon and dimethyl sulfoxide.

14. The process of claim 9 wherein reaction step a) is carried out at 70° C. to 150° C.

15. The process of claim 10 wherein $R_1$ is $C_4$–$C_6$alkyl.

16. A process for the preparation of a compound of formula I

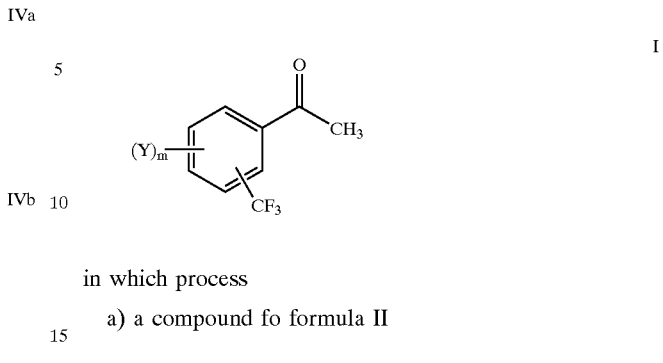

in which process a) a compound fo formula II

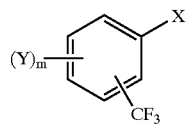

wherein

X is chlorine, bromine or iodine, is reacted with a vinylether of formula IIIa or an enamide of formula IIIb $CH_2$=$CH$—$OR_1$ (IIIa)

$CH_2$=$CH$—$N(R_2)$—$CO$—$R_3$ (IIIb)

wherein $R_1$ and $R_2$ are each independently of the other $C_1$–$C_8$alkyl, $C_2$–$C_8$alkenyl, $C_1$–$C_8$alkoxyalkyl, $C_3$–$C_6$cycloalkyl, phenyl-$C_1$–$C_2$alkyl or $C_1$–$C_8$acyl, and $R_3$ is $C_1$–$C_8$alkyl, $C_1$–$C_8$alkenyl, $C_1$–$C_8$alkoxyalkyl, $C_3$–$C_6$cycloalkyl or phenyl-$C_1$–$C_2$alkyl, in a solvent, in the presence of a base and of a catalytic amount of a palladium compound and a monodental or bidental phosphine ligand;

b) the resulting intermediate of formula IVa and IVb

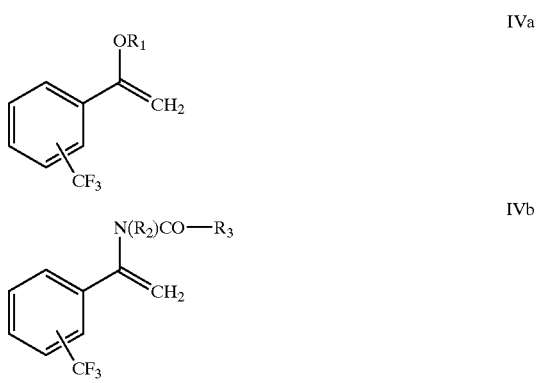

is hydrolyzed to the compound of formula I.

17. The process of claim 16 wherein X is bromine.

* * * * *